_United States Patent_ [19]

Stringer et al.

[11] 4,046,661
[45] Sept. 6, 1977

[54] CERAMIC OXYGEN PROBE

[75] Inventors: Robert Kenneth Stringer, Heidelberg; Kenneth Alan Johnston, Elsternwick, both of Australia

[73] Assignee: Commonwealth Scientific and Industrial Research Organization, Campbell, Australia

[21] Appl. No.: 243,930

[22] Filed: Apr. 14, 1972

[30] Foreign Application Priority Data

Apr. 14, 1971 Australia ............... 4587/71

[51] Int. Cl.² ........................................... G01N 27/46
[52] U.S. Cl. ........................... 204/195 S; 204/1 T; 264/61
[58] Field of Search ................. 204/1 T, 195 S

[56] References Cited
U.S. PATENT DOCUMENTS

| 3,464,008 | 8/1969 | Meysson et al. | 204/195 S |
| 3,616,407 | 10/1971 | Engell et al. | 204/195 S |
| 3,619,381 | 11/1971 | Fitterer | 204/1 T |
| 3,723,279 | 3/1973 | Fruehan et al. | 204/195 S |

FOREIGN PATENT DOCUMENTS

| 2,042,249 | 3/1971 | Germany | 204/195 S |
| 2,035,882 | 2/1971 | Germany | 204/195 S |
| 1,191,222 | 5/1970 | United Kingdom | 204/195 S |

_Primary Examiner_—T. Tung
_Attorney, Agent, or Firm_—Sughrue, Rothwell, Mion, Zinn and Macpeak

[57] ABSTRACT

A probe for use in measuring the oxygen concentration of fluids comprising a disc or pellet of solid electrolyte located at or near the end of a ceramic tube, and an electrode within the tube contacting the inner face of the pellet, characterized in that the ceramic tube is constructed of alumina, mullite or an aluminous porcelain containing at least 4 per cent by weight of free alumina and not more than 40 per cent by weight silica, and the electrolyte is sealed to the tube by a fusion weld.

3 Claims, 2 Drawing Figures

CERAMIC OXYGEN PROBE

This invention relates to improvements in apparatus for measuring the amount of oxygen contained in a fluid in a continuous manner by an electrochemical process. The invention is concerned principally with probes for use in the measurement of the oxygen content in molten metals but it is useful also in the determination of oxygen in liquids and gases of all types, for example, chemical liquids, such as those encountered in the paper industry and in extractive metallurgy, and furnace atmospheres. The invention finds application in processes of metal manufacture where the percentage of oxygen in the metal produced is critical and is thus particularly suited to the measurement of oxygen in copper and its alloys.

Sensing devices in the form of probes, in which a plug of solid electrolyte is supported at or near the end of a tube, are known. Measurement of the e.m.f. generated across the electrolyte, when the outer face is in contact with the fluid being tested and the other face with a system in which the oxygen potential is controlled at a constant value, gives an indication of the oxygen content of the fluid. For example, when the outer face of the electrolyte material contacts molten copper and the other face is placed in contact with a reference electrode working with a known oxygen pressure, for instance with the known mixture nickel-nickel oxide or with an appropriate oxygen-containing gas mixture, and connected with a current collector, another current collector being immersed in the liquid copper, the measurement of the voltage E between the two current collectors makes it possible to establish the percentage of oxygen in the liquid metal by use of the formula:

$$E = \frac{RT}{nF} \ln_e \frac{pO_2(\text{liquid metal})}{pO_2(\text{reference})}$$

in which
$R$ = the gas constant
$T$ = the absolute temperature
$n$ = the number of electrons transferred per oxygen molecule, equal to 4
$F$ = the value of a Faraday
$P$ = the partial oxygen pressure, and the known relationship between oxygen pressure and oxygen concentration for the liquid metal concerned.

The said voltage may be measured by a suitable electrical device, e.g. an electrometer, the impedance of which is sufficiently high relative to that of the measuring cell.

Examples of such probes are described in the specifications of U.S. Pat. Nos. 3,468,780, 3,616,407 and 3,619,381, and British Pat. No. 1,254,060. In addition, J. K. Pargeter, in the October, 1968 issue of the Journal of Metals, at page 27, has described probes of this nature, as has R. G. H. Record in his paper given at the Fourth Industrial Process Heating Conference, Manchester, 1969, and published in Instrument Practice, March, 1970 at page 161. Other probes which operate on the same principle have been described in the specifications of U.S. Pat. Nos. 3,578,578 and 3,630,874, and Australian Pat. No. 422,765 and in the extensive bibliography listed in the introduction to U.S. Pat. No. 3,619,381 by G. R. Fitterer. As Fitterer had pointed out, most of these probes are not suitable for use with molten metals at the temperature of molten steel, either because they are not able to withstand the thermal shock of immersion into the molten metal, or because the seal between the electrolyte and the tube is unsatisfactory and molten metal leaks into the tube. To overcome these problems, Fitterer uses a small pellet of electrolyte sintered into a silica tube and claims success in molten steel. However, our attempts to use this type of probe in molten copper were unsuccessful. Investigation of the probes showed extensive cracking even before it was used, which suggests that on cooling after constructing the probe, the difference in coefficients of thermal expansion of silica and the electrolyte (zirconium oxide) is such that stresses set up within the electrolyte and tube cause the cracking. We believe that the probe is useful at liquid steel temperatures (1600° to 1650° C) because (i) the plug of electrolyte expands to close the cracks and (ii) the silica is plastic at these temperatures and the pressure of the surrounding molten metal on the immersed probe produces, in effect, a compression seal around the zirconia pellet. However, at lower temperatures, e.g. in molten copper the fused quartz is rigid and the weak mechanical seal between the components may allow penetration of molten copper and/or gas along the zirconia-quartz interface. Pargeter has also realised the unsuitability of such a probe at temperatures below molten steel, and comments (loc. cit.):

"As quartz and zirconia do not 'wet', a mechanical joint is obtained rather than a true fused joint. However, on insertion into molten steel, the softening of the quartz and expansion of the zirconia produces a joint which withholds the steel".

One approach to the solution of these problems is described in Australian patent application No. 49,038/69 which discloses a probe in which the conventional fused quartz tube is replaced by a tube of a metal, a refractory alloy or a cermet into one end of which a zirconia cup is cemented. Examples of suitable tube materials are given as ferritic steel, iron, kanthal, and the cermet chromium/alumina. In this arrangement, however, the tube is used as the contact electrode with the molten metal and for this reason, as well as for structural reasons, the zirconia cup must be cermented into the tube with a non-conducting cement. A considerable thickness of the cement must be used to overcome the effects of differential expansion. To this end also, the disclosure shows the use of a ring of refractory material interposed in the cement layer between the sensing element and the conducting tube. This arrangement is also stated to give the joint better resistance to penetration by liquid metal, but construction of the probe is a complex matter and the probes are consequently expensive.

It is an object of the present invention to provide an oxygen probe in which a fluid-tight seal between the electrolyte and the tube is simply achieved for temperatures up to and including that of molten steel.

Essentially, it has been found that this objective is achieved by a probe in which the electrolyte pellet is fusion welded to a tube of alumina, mullite, or an aluminous porcelain preferably containing free alumina. The true weld, involving the formation of a eutectic liquid at the electrolyte/tube interface is a good seal having substantial strength, and the coefficients of thermal expansion of the usual zirconia electrolytes — and related materials — are sufficiently similar to those of the tube materials, so that much less stress is experienced in the materials of the probe on cooling after fabrication and the probe end remains impermeable to the fluid being investigated for long enough to determine the oxygen concentration over a period of several days.

According to the present invention, therefore, a ceramic oxygen probe comprises a disc or pellet of solid electrolyte located at or near the end of a ceramic tube, and an electrode contacting the inner surface of the pellet, characterised in that the ceramic tube is constructed of alumina, mullite, or an aluminous porcelain containing at least 56% by weight of alumina, and in which at least 7 percent of the alumina content is free alumina, and not more than 40 percent by weight silica, and the electrolyte is sealed into the tube by a fusion weld.

Also according to the present invention, a method of constructing a probe as described in the last preceding paragraph comprises locating the pellet of electrolyte in the end of the ceramic tube and forming a fusion weld between the electrolyte and tube by the steps of (i) heating the tube end in a refractory tunnel enclosure to a temperature of about 1650° C, (ii) using an oxygen-acetylene flame directed on to the tube end to raise the temperature of the tube material sufficiently to cause a melting reaction between the tube and the electrolyte, then (iii) allowing the tube to cool in the refractory tunnel.

The preferred solid electrolytes are thoria, doped with yttria, and stabilised or partially stabilised zirconia and hafnia.

A temperature in excess of 1720° C is necessary to achieve a proper fusion weld between the alumina-containing ceramic tube and a zirconia electrolyte. It is preferred to provide the fusion weld by direct contact and interaction between the component materials, but it is within the scope of the invention to assist in the formation of the weld by applying a paste of the major components of the eutectic compound, mixed in the appropriate quantities, to the surface being welded.

If the tube of the probe is aluminous porcelain, it is necessary that this material contains at least 4 percent by weight of chemically unbound (free) alumina to ensure that a good seal is obtained. With less than 4 percent free alumina, good seals are not obtained by fusion welding. Preferably, the aluminous porcelain contains between 5 and 10 percent of free alumina. It is also essential for a good seal that the aluminous porcelain contains no more than 40 percent silica by weight. Good seals have been obtained with tube of aluminous porcelain containing less than 40 percent by weight silica, but with tubes having more than 40 percent silica by weight, the seals produced have not been as reliable.

Figure 1:
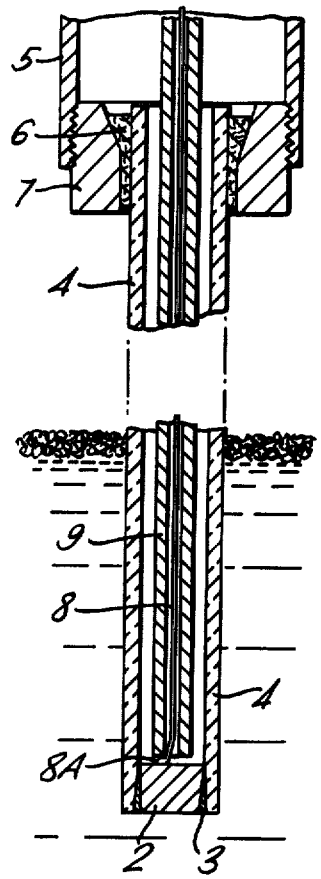
FIG. 1 is a sectional view of the probe of the present invention.
Figure 2:
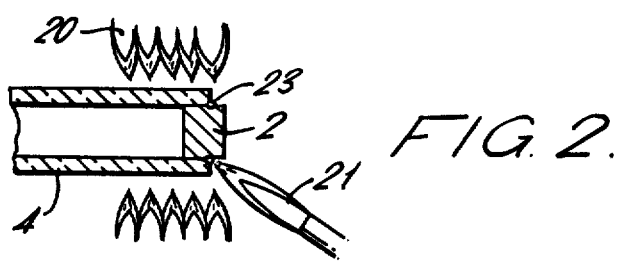
FIG. 2 illustrates the technique used in effecting the fusion weld.

As shown in FIG. 1, a plug of electrolyte 2 is sealed by a fusion weld 3 into the end of ceramic tube 4, which is of mullite, aluminous porcelain containing free alumina, or alumina. The ceramic tube 4 is about 50 cm long and at its other end is supported in a stainless steel tube 5 using a seal of asbestos fibre 6, compressed by an externally threaded nut 7 having a tapered bore, which is screwed into the threaded end of tube 5. The inner electrode of the probe is a platinum wire 8 which passes through the centre of a narrow bore alumina tube 9, having typical dimensions: outside diameter — 3 mm, bore 1 mm. The platinum wire 8 is held in contact with the inner face of electrolyte 2 by pressure on the alumina tube 9 from a spring (not shown) in the stainless steel tube 5. The wire 8 is formed into a lump 8A at its end, which serves to space the tube 9 from electrolyte 2 so that a reference gas, usually air, can be pumped through tube 9 to the interior of the probe at the inner surface of the electrolyte. In use, the tube 4 is inserted into a fluid to a depth of 8 to 10 cm.

In constructing the probe, the seal between the electrolyte and tube is established by rotating the tube 4 held with its axis horizontally, in a refractory tunnel heated by natural gas — oxygen flames 20. The electrolyte plug 2 is usually inserted into the end of the tube with a portion protruding. After pre-heating to 1600°-1650° C, oxygen-acetylene flame 21, usually from a hand-held burner, forms a small pool of liquid material 23. This liquid is caused to flow around the electrolyte plug until liquid material surrounds the plug 2 at the end of tube 4. At this stage, the plug is sucked into the tube 4 by forces thought to be derived from surface tension and capillary movement of the eutectic liquid at the electrolyte/tube interface. (If too much heat is used, the pellet of electrolyte can be sucked into the body of the tube 4, which should be avoided). The end of the tube and plug are usually ground to provide a clean outer surface of the probe.

If the tube is alumina, the pool of liquid is difficult to detect, and in this case the movement of the plug into the tube indicates that the eutectic liquid has been formed and a satisfactory seal will be obtained. In fact, we have used a tube 4 having an internal diameter less than the outer diameter of the plug 2, ground so that the plug can be only half-inserted into the tube. Full insertion of the plug can only be achieved when the eutectic liquid is formed. By this technique, a good seal can invariably be achieved, providing overheating does not occur with consequential travel of the electrolyte plug into the body of the tube.

A separate contact electrode, also of platinum or other suitable metal or composite material, such as a chrome-alumina cermet is used to provide electrical connection with the fluid medium under test. In the event that the probe is to be used in gases or electrically insulating liquids, the second electrode must contact the outer face of the electrolyte pellet. In other situations, the second electrode can be separate to the probe, though it is preferably located near to it.

Solid electrolyte pellet materials, because of low thermal conductivities and moderately high expansion coefficients, are prone to thermal shock. The liability to thermal shock decreases, however, as the dimensions of the body become smaller. In the present invention, the type of construction employed, in which a small electrolyte disc is sealed into the end of a small-bore refractory tube, permits the construction of a device with a minimum volume of the thermal shock-prone material. Other advantages of the device of the present invention are:

1. Simplicity and speed of construction
2. The possibility of re-use of the relatively expensive refractory tube component when the electrolyte does fail.
3. Freedom from porosity of the seal at temperatures below 1450° C such as in molten copper, permitting accurate readings to be obtained.
4. The use of a refractory seal, particularly that formed between alumina and zirconia, which permits use of the device in higher melting point metals such as iron, steel and nickel.

The construction, use and advantages of the device described above will be further elucidated in the following examples.

EXAMPLE 1

A cylindrical pellet of zirconia stabilised with yttria and with dimensions 5.1 to 5.2mm diameter and 3 to 5mm long was placed in the end of an alumina tube, nominally of 8mm outside diameter and 5mm bore; which end had been machined to provide a clearance of 0.03 to 0.05mm on the pellet diameter.

The tube end was heated slowly by a natural gas-oxygen flame within a refractory tunnel enclosure to a temperature of approximately 1650°–1700° C. At the same time the tube was rotated at approximately 40 rpm to ensure uniformity of heating. An oxygen-acetylene flame was then directed onto the tube end while still in the enclosure and the temperature raised until the melting reaction described above was observed to occur. The oxygen-acetylene flame was then removed and the gas oxygen-flame lowered slowly and then turned off. The probe device was then allowed to cool within the refractory tunnel. When cool the end of the device was ground until the electrolyte surface was flush with the tube end.

EXAMPLE 2

The procedure of Example 1 was repeated using a pellet of magnesia stabilised zirconia.

EXAMPLE 3

The procedure of Example 1 was repeated except that a tapered joint was formed initially between the pellet and tube. The pellet was ground in the form of a frustum of a cone with 2° to 4° apex angle, and a matching tapered socket was ground into the end of the alumina tube. The pellet and tube were lapped together with boron carbide grit. The fusion welding procedure was as described in Example 1.

EXAMPLE 4

A cylindrical pellet of zirconia, stabilised with CaO, with dimensions 5.1 to 5.2 mm diameter and 3–5 mm long was placed in the end of an aluminous porcelain tube of nominal 8mm outside diameter and 5 mm bore, machined out if necessary to provide a suitable clearance between the tube and pellet. (Because significant flow of the liquid tube material occurs, the clearance was found not to be critical).

The tube end was heated slowly by a natural gas-oxygen flame within a refractory tunnel enclosure to a temperature of approximately 1650° C. At the same time the tube was rotated at approximately 40 rpm to ensure uniform heating. A flame of oxygen-acetylene was directed onto the tube end, while still in the enclosure, and the temperature increased until the tube material melted and flowed on to the surface of the pellet. Both flames were removed and the device was allowed to cool in the refractory tunnel.

Where flow of the tube material onto the outer face of the pellet had occurred the end of the device was ground back to expose the pellet.

EXAMPLE 5

The procedure of Example 4 was repeated with:
1. A mullite tube substituted for the aluminous porcelain.
2. Zirconia stabilised, or partially stabilised with (a) magnesia (MgO), (b) yttria ($Y_2O_3$) or (c) scandia ($Sc_2O_3$), substituted for Zirconia stabilised with lime(-CaO).

In each of the above Examples, liquid-tight, mechanically sound seals were obtained in which there was clear evidence of "wetting" between the solid electrolyte pellet and the surrounding tube.

The sensing devices produced in the above Examples were used under normal operating conditions in the determination of the oxygen content of molten copper in both anode and wire-bar casting operations. The electrical performance, reliability and accuracy of the sensing devices of this invention were at least as good as those of a conventional probe and the useful life of the new probes was also at least as long as the conventional probes. The cheapness and ease of construction of the sensing devices of the present invention, together with their promise of longer useful life offer clear advantages over the prior art devices.

We claim:

1. A probe for use in measuring the oxygen concentration of fluids comprising: a ceramic tube constructed of alumina, mullite, or an aluminous porcelain containing at least 56% by weight alumina and in which at least 7% of the alumina content is free alumina and not more than 40% by weight silica; a pellet of solid electrolyte located in said ceramic tube in proximity to the end of said ceramic tube, and sealed to the tube by a fusion weld, the outer diameter of said pellet being substantially the same as the inner diameter of said tube; a eutectic mixture at the electrolyte/tube interface; and an electrode within said tube contacting the inner face of said pellet.

2. A probe as defined in claim 1, in which the electrolyte is doped thoria, stabilized zirconia, partially stabilized zirconia, stabilized hafnia, or partially stabilized hafnia.

3. A probe as defined in claim 1 including a front electrode contacting the outer face of the electrolyte pellet.

* * * * *